United States Patent
Schauer

(10) Patent No.: US 9,968,703 B1
(45) Date of Patent: May 15, 2018

(54) BURN WOUND COMPOSITION AND METHODS FOR TREATING BURN WOUNDS

(71) Applicant: Roland C. Schauer, Havre De Grace, MD (US)

(72) Inventor: Roland C. Schauer, Havre De Grace, MD (US)

(*) Notice: Subject to any disclaimer, the term of this patent is extended or adjusted under 35 U.S.C. 154(b) by 0 days. days.

(21) Appl. No.: 15/624,627

(22) Filed: Jun. 15, 2017

(51) Int. Cl.
| | |
|---|---|
| *A61L 15/40* | (2006.01) |
| *A61L 15/44* | (2006.01) |
| *A61K 36/886* | (2006.01) |
| *A61L 15/34* | (2006.01) |
| *A61K 36/15* | (2006.01) |

(52) U.S. Cl.
CPC .......... *A61L 15/40* (2013.01); *A61K 36/15* (2013.01); *A61K 36/886* (2013.01); *A61L 15/34* (2013.01); *A61L 15/44* (2013.01)

(58) Field of Classification Search
CPC ....... A61K 36/15; A61K 36/886; A61L 15/40; A61L 15/34; A61L 15/44; A61L 26/0057
See application file for complete search history.

(56) References Cited

U.S. PATENT DOCUMENTS

| | | | |
|---|---|---|---|
| 3,943,248 A * | 3/1976 | Shulman | A61K 31/355 424/195.18 |
| 5,997,876 A | 12/1999 | Shikhashvili et al. | |
| 8,784,892 B2 | 7/2014 | Touitou | |
| 8,858,988 B2 | 10/2014 | Chamberland et al. | |
| 8,992,995 B2 * | 3/2015 | Penney | A61K 8/27 424/537 |
| 2012/0015041 A1 | 1/2012 | Sun | |
| 2012/0308637 A1 | 12/2012 | Chamberland et al. | |

FOREIGN PATENT DOCUMENTS

| | | | |
|---|---|---|---|
| EP | 0967988 B1 | 4/2002 | |
| EP | 1265625 B1 | 12/2004 | |
| WO | WO-9843613 A1 * | 10/1998 | ........... A61K 9/0014 |
| WO | WO 2001/052872 A2 | 7/2001 | |
| WO | WO 2002/089846 A1 | 11/2002 | |
| WO | WO 2011/054090 A1 | 5/2011 | |
| WO | WO 2012/129683 A1 | 10/2012 | |

OTHER PUBLICATIONS

Surjushe, et al. "Aloe Vera: A Short Review," Indian Journal of Dermatology, 2006; 53(4)163-168; Taken from http://www.ncbi.nlm.nih.gov/pmc/articlesPMC2763764/?report=printable, printed Jul. 14, 2016.
Kuznesof, "Beeswax," Chemical and Technical Assessment 65th JECFA, 6 pages.

* cited by examiner

*Primary Examiner* — Michael B. Pallay
(74) *Attorney, Agent, or Firm* — K&L Gates LLP

(57) ABSTRACT

Burn wound compositions containing leaf lard, yellow beeswax, Oil of Spike, pine rosin, and *aloe vera* are described for treatment of first, second, and third degree burn wounds.

20 Claims, No Drawings

BURN WOUND COMPOSITION AND METHODS FOR TREATING BURN WOUNDS

FIELD OF INVENTION

The present invention relates in general to compositions and methods used for treating burn wounds.

BACKGROUND OF THE INVENTION

Local treatment of burns often includes cleansing and debridement, topical antimicrobial agents, and dressings. In fact, the healing of a burn wound is a dynamic process and local management may vary with the evolving clinical picture. Conservative, non-operative therapies include cleansing, debridement, topical antimicrobial drugs, and dressing changes.

A disadvantage of antibiotic treatment for burn wounds is that bacteria often develop tolerance and resistance to the medication over time, and thus become difficult to eradicate. For example, *Staphylococcus aureus* has become resistant to many commonly used antibiotics. As a result antibiotic resistant *Staphylococcus*-strains are a serious problem in hospitals. Therefore, there is a need for alternative burn wound compositions to effectuate healing of burn wounds and to prevent invasive sepsis.

BRIEF SUMMARY OF THE INVENTION

The invention described in this specification generally relates to compositions and methods for treating burn wounds. The compositions can comprise leaf lard, yellow beeswax, Oil of Spike, pine rosin, and *aloe vera* extract. The invention described in this specification also relates to methods of making a burn wound composition, where the burn wound composition includes leaf lard, yellow beeswax, Oil of Spike, pine rosin, and aloe vera extract. The invention described in this specification also relates to methods of treating a burn wound including applying to a burn wound a burn wound composition, wherein the burn wound composition includes leaf lard, yellow beeswax, Oil of Spike, pine rosin, and aloe vera extract.

In one example, a burn wound composition consists of, in percent by total composition weight, 46% to 56% leaf lard derived from pigs of the species *Sus scrofa domesticus*, 5% to 15% yellow beeswax derived from honey bees of the genus *Apis*, 0.5% to 5% Oil of Spike derived from *Lavandula latifolia*, 25% to 35% pine rosin derived from southern yellow pine trees of the genus *Pinus*; and 0.1% to 10% *aloe vera* extract derived from Aloe Barbadensis Miller.

In another example, a burn wound composition consists of leaf lard, yellow beeswax, Oil of Spike, pine rosin, and *aloe vera*.

In another example, a method of making a burn wound composition including leaf lard, yellow beeswax, Oil of Spike, pine rosin, and *aloe vera* comprises melting the leaf lard in a container over a heat source, dissolving the yellow beeswax into the melted leaf lard to form a first mixture, mixing the pine rosin into the first mixture comprising the yellow beeswax and the leaf lard to form a second mixture, and adding the Oil of Spike and the *aloe vera* to the second mixture by stirring to form the burn wound composition.

In another example, a method of treating a burn wound comprises applying to a burn wound a first layer of a burn wound composition including leaf lard, yellow beeswax, Oil of Spike, pine rosin, and *aloe vera*, applying to the burn wound a second layer of the burn wound composition, and not covering the burn wound or the applied first and second layers of the burn wound composition.

DETAILED DESCRIPTION OF THE INVENTION

The composition and methods described in this specification can comprise a burn wound composition for treatment of first, second, and third degree burns to mammalian tissue. The burn wound to mammalian tissue may be from any heat source. For example, the source of the burn wound may be from heat (including high temperature solids, liquids, and gases that contact tissue), flame, chemicals, electrical power, steam, radiation, or the like, or any combination thereof. The burn wound composition works to relieve topical and subtopical pain within minutes of application of the composition to the burn wound and heals burn wounds without disfiguration to the skin. For example, the burn wound composition may provide pain relief in greater than 3 three minutes, greater than 5 minutes, in a range of 5 to 10 minutes, in a range of 5 to 15 minutes, in about 10 minutes, in a range of 5 to 20 minutes, or in less than a half hour of application of the burn wound composition to the burn wound, depending on the type and degree of the burn wound.

Where the application of the burn wound composition is within hours of obtaining the burn wound, the burn wound composition eliminates pain and begins the healing process of the burn wound. For example, when the burn wound composition is applied to the burn wound within twenty four hours of the burning of the tissue, the burn wound composition will substantially eliminate pain and heal the epidermis of first degree skin damage and eliminate blistering from second and third degree burns. In certain embodiments, where the burn wound composition is used within five minutes of a tissue burn it will eliminate pain within five or ten minutes and obviate blisters within two hours leaving the skin supple, undamaged, and its natural color. In certain embodiments, involving blistering and more severe burn wounds, reaction time for pain elimination and healing may take longer. For example, where the burn wound is more severe, such as a third degree or chemical burn causing blistering, the blisters will diminish somewhat and/or disappear within 24 hours of application of the burn wound composition to the burn wound.

In certain embodiments, where a burn wound is instantaneously caused from radiant heat (e.g., a hot muffler), flame (e.g., propane torch), steam (e.g., scald from boiling water), chemicals (e.g., paint thinner), boiling water, electricity (e.g., 120 volts maintaining twenty amps), heated metal (e.g., cooking utensil), or the like, or any combination thereof, the burn wound composition should to be applied before blistering occurs. Typically, the burn wound composition is applied within five to ten minutes of the burning of the tissue, depending on the type and degree of the burn.

In certain embodiments, burn wounds resulting from chemicals such as hydrochloric acid, sodium hydroxide, oxidants, and solvents including acetone, paint thinners (e.g., lacquer thinner, turpentine, and mineral spirits), methyl acetate, hexane, and petroleum distillates; or radiation burns from such sources as radiation therapy, ultraviolet light (the sun or tanning beds), infrared radiation, and possibly radio frequency energy can be treated by application of the burn wound composition at the time the burn is recognized.

The inventor was surprised to observe that the burn wound composition is found to heal and eliminate pain consistently when applied to burn wounds and unequivocally works to eliminate or reduce the pain, redness, and blistering, when applied to the burn wound within minutes of burning of the tissue. Time and time again, the inventor, unexpectedly and consistently, observed healing of a burn wound substantially without blemish to the skin following application of the soft burn wound composition to the burn wound.

The inventor was surprised to find that this soft burn wound composition does not require prior cleansing of the wound before application and can be applied without a bandage directly to the burn wound without causing discomfort to the burn victim. Without intending to be bound by theory or hypothesis, the inventor attributes this surprising and unexpected effect to the fact that the burn wound composition does not produce a cooling effect on the skin, as found in many conventional burn wound compositions. Most conventional "burn salves" provide only minimal treatment of the burn wound. One must use several conventional products for different types of burns to achieve what the present burn wound composition does in one composition. Therefore, the present composition eliminates the cost and inconvenience of having to have on hand a variety of different conventional burn treatment products. The savings in medical costs resulting from on-the-spot treatment of all types and degrees of burns with the present burn wound composition can be substantial. Individuals can afford to carry one burn wound composition instead of several different conventional products, creams, and salves.

The burn wound composition can comprise leaf lard, beeswax, Oil of Spike, rosin, and *aloe vera*. In certain embodiments, the burn wound composition can comprise, by total weight percent of the burn wound composition, at least 30% leaf lard, 5% to 15% yellow beeswax, 0.5% to 10% Oil of Spike, 20% to 40% pine rosin, and 0.1% to 10% *aloe vera*.

In certain embodiments, the burn wound composition can comprise, by weight percent, based on the total weight of the burn wound composition, 46% to 56% leaf lard derived from pigs of the species *Sus scrofa domesticus,* 5% to 15% yellow beeswax derived from honey bees of the genus Apis, 0.5% to 5% Oil of Spike derived from *Lavandula latifolia,* 25% to 35% pine rosin derived from southern yellow pine trees of the genus *Pinus*, and 0.1% to 10% *aloe vera* extract derived from *Aloe Barbadensis Miller.* In certain embodiments, the burn wound composition can comprise, by weight percent based on the total weight of the burn wound composition, 49% to 53% leaf lard derived from pigs of the species *Sus scrofa domesticus,* 8% to 12% yellow beeswax derived from honey bees of the genus *Apis,* 1% to 4% Oil of Spike derived from *Lavandula latifolia,* 28% to 33% pine rosin derived from southern yellow pine trees of the genus *Pinus*, and 3% to 7% *aloe vera* extract derived from Aloe Barbadensis Miller.

Leaf Lard. The leaf lard used in the burn wound composition can consist of leaf lard derived from pigs of the species *Sus scrofa domesticus* or Sus *domesticus*. Pure leaf lard comes from the family Suidae, a family of artiodactyl mammals commonly called Pig, Hog, Boar, Pork, or Swine. In the burn wound composition, leaf lard is essentially a skin conditioner and moisturizer, keeping the flesh supple and moist while the other ingredients work to heal, but rich in vitamin D, it is known for its ability to heal the epidermis. Only pigs that have access to sunshine have vitamin D in the lard derived from them. Thus, leaf lard including vitamin D promotes cell growth, neuromuscular and immune function, and reduces inflammation. Other components in leaf lard supplement the healing process of the burn wound composition. For example, leaf lard contains Omega-3 fatty acids known to help with blood clotting and inflammation and choline that aids in the rejuvenation of the skin during the healing process.

White leaf lard is "pure" leaf lard, as used in this specification, meaning without any extraneous components added to it during or after rendering. As used in this specification, the term "rendering" or "rendered" refers to the action of obtaining lard or pig fat from any part of the pig where there is a high proportion of adipose tissue. The lard can be "rendered" by steaming or boiling the tissue in water and then separating the insoluble fat from the water, or by the use of dry heat. White leaf lard is the highest grade of lard. White leaf lard is heat stable thereby giving the mixture a very long shelf life. White leaf lard comes from the visceral, or soft, fat from around the kidneys and loin of the pig. White leaf lard has a very soft, spreadable consistency at room temperature (25° C.). The white leaf lard used in the burn wound composition may be obtained from grain fed pigs raised under organic, free-range conditions in eastern Pennsylvania in the United States, for example.

In certain embodiments, leaf lard used in the burn wound composition may include, by weight percent, based on the total weight of the burn wound composition, at least 70% or any sub-range subsumed therein, such as for example, at least 20%, at least 30%, at least 40%, at least 50%, at least 60%, 40% to 60%, 46% to 56%, and 49% to 53%. In certain embodiments, leaf lard used in the burn wound composition may include, by weight percent, based on the total weight of the burn wound composition, 30%, 40%, 45%, 50%, 51%, 51.3%, 51.5%, 55%, 56%, 60%, or 70%.

Yellow Beeswax. The yellow beeswax (Cera alba from the genus Apis) is used in the burn wound composition because it provides a protection against irritation while still allowing the skin to breathe. The yellow beeswax also offers anti-inflammatory, antibacterial, antiviral, anti-allergenic, and germicidal antioxidant properties suitable for wound healing and making it helpful in treating skin irritation. Beeswax is also known for locking in moisture (from the leaf lard), protecting skin from environmental factors and fostering growth of skin cells. Because of its moisture locking properties, yellow beeswax is naturally nourishing as it contains vitamin A and effectively softens skin tissue. The function of the yellow beeswax within the burn wound composition is to promote the healing process, keep the burn wound composition from dissipating too quickly, and to maintain the burn wound composition in place on the burn wound.

Yellow beeswax, as used in the burn wound composition, is pure as it has not been bleached (like white beeswax) or processed. The beeswax used in the burn wound composition can be obtained from sources in eastern Pennsylvania in the United States thereby making it different from beeswax from other regions having different flora.

In certain embodiments, yellow beeswax used in the burn wound composition may include, by weight percent, based on the total weight of the burn wound composition, up to 25% or any sub-range subsumed therein, such as for example, from 3% to 25%, from 5% to 20%, from 7% to 15%, and from 8% to 13%. In certain embodiments, yellow beeswax used in the burn wound composition may include, by weight percent, based on the total weight of the burn wound composition, 9%, 10%, 10.3%, 10.5%, 10.8%, 11%, 12%, 13%, 14%, or 15%.

Oil of Spike. Oil of Spike, as used in the burn wound composition, is the oil derived from the Spike Lavender plant, *Lavandula latifolia*, cultivated in Portugal and produced through steam or water distillation. The Portuguese soil composition and climate is unique and thereby provides the oil with properties different from oil derived from *Lavandula latifolia* cultivated in other regions. Oil of Spike is anti-microbial, anti-inflammatory, antiseptic, anti-viral, and has anti-infection properties that help to soothe and heal burns.

The inventor has observed that Oil of Spike as an ingredient in the burn wound composition eliminates pain in burn wounds. Oil of Spike is also found to relax the body in the presence of pain by reducing anxiety levels due to its absorption through the skin and detection by the olfactory senses. A calm mental state induced by the Oil of Spike makes pain more bearable, lessening its impact by reducing the perception of pain from the burn wound.

Oil of Spike from *Lavandula latifolia*, contains more camphor than other species of the Lavender family, Lamiaceae, such as *Lavandula angustifolia*. Indeed, one of the major constituents of Oil of Spike is camphor, a counter irritant known for its analgesic use to ease aches and pains, but contraindicated for burn treatments. Thus, the inventor unexpectedly found that, even in view of its stronger camphor content, Oil of Spike (also known as spike lavender) provided more potent analgesic and expectorant properties than other species of lavender.

In certain embodiments, Oil of Spike used in the burn wound composition may include, by weight percent, based on the total weight of the burn wound composition, from 0.1% to 10%, or any sub-range subsumed therein, such as for example, from 0.3% to 3%, from 1% to 4%, from 1.5% to 2.5%, or from 1.75% to 2.25%. In certain embodiments, Oil of Spike used in the burn wound composition may include, by weight percent, based on the total weight of the burn wound composition, 2%, 2.2%, 2.3%, 2.4%, 2.5%, 2.6%, 2.7% 2.8%, 2.9%, 3%, 4%, 5%, 6%, 7%, or 8%.

Pine Rosin. Pine gum rosin, as used in the burn wound composition has several natural medicinal actions: antiseptic, anti-infection, antifungal, antidiabetic, neurotonic, decongestant of the lymphatic system, parasiticide, antimicrobial, and anti-catarrhal. Therefore pine rosin is useful as an antiseptic for killing bacteria that may be present in the burn wound as well as preventing any bacterial growth or infection that could otherwise occur.

The pine rosin helps the burn wound composition maintain an airtight "bandage". The pine rosin acts as a binder for the ingredients of the burn wound composition that statically maintains the burn wound composition in place in contact with the burn wound. Thus, the pine rosin provides a barrier to airborne bacteria while drawing out toxins and poisons that may have resulted from certain types of burns. The pine rosin further acts as a counter irritant by increasing the flow of white blood cells to the infected area, heightening the body's own immune response and eliminating pain. The fragrance of the pine rosin also provides relief in the form of a calming agent.

In certain embodiments, the pine rosin used in the burn wound composition is derived from yellow southern pine (loblolly pine, longleaf pine, shortleaf pine, and slash pines) grown in the southern United States, specifically in Georgia. The pine rosin can consist of rosin derived from at least one of *Pinus taeda* (loblolly pine), *Pinus palustris* (longleaf pine), *Pinus echinata* (shortleaf pine), and *Pinus elliottii* (slash pine). These pines are grown in soil unique to that region thereby giving the pine rosin different properties than yellow pine grown in other locations or regions. For example, the soil in Georgia, U.S., skews the pH balance of the plants that grow in the soil to a higher acidity thereby altering its chemical composition. Moreover, the practical melting point of pine rosin varies with different specimens. The pine rosin used in the burn wound composition is derived from yellow southern pine from Georgia in the United States containing many different components than those found in a hemlock pine or a juniper plant found in Asia. Thus, pine rosin derived from the yellow southern pine affords many different healing properties not found in rosin derived from other conifers in different environments, climates, flora, and soil content.

In certain embodiments, pine rosin used in the burn wound composition may include, by weight percent, based on the total weight of the burn wound composition, from 25% to 35%, or any sub-range subsumed therein, such as for example, from 28% to 33%, from 29% to 32%, or from 29% to 31%. In certain embodiments, pine rosin used in the burn wound composition may include, by weight percent, based on the total weight of the burn wound composition, 29%, 30%, 30.5%, 30.8%, 31%, 31.5%, 32%, 33%, 34%, 35%, 36%, 37%, 38%, 39%, or 40%.

Aloe Vera. Aloe Vera (*Aloe Barbadensis Miller* or *Aloe Barbadensis Mill*) is a succulent plant species. As used herein, the term "*aloe vera*" refers to an extract of the *aloe vera* plant. Extract derived from *Aloe Barbadensis Miller*, as used in the burn wound composition, includes many vitamins and minerals that have rejuvenating healing and soothing properties. For example, extract derived from *Aloe Barbadensis Miller* contains large amounts of vitamins including vitamins A, B1, B2, B3, B6, C, and E. Extract derived from *Aloe Barbadensis Miller* is also rich in choline and folic acid, all of which help the skin regenerate and remain healthy. Minerals found in extract derived from *Aloe Barbadensis Miller* are abundant as well, including calcium, iron, potassium, copper, manganese, selenium, sodium, and chromium. These vitamins and minerals within the extract derived from *Aloe Barbadensis Miller* boost the healing and pain relieving properties of the other ingredients. Thus, extract derived from *Aloe Barbadensis Miller* reduces inflammation of the epidermis, dermis, and hypodermis.

Moreover, extract derived from *Aloe Barbadensis Miller* is a remedy for skin conditions including burns, and sunburn. Extract derived from *Aloe Barbadensis Miller* neutralizes the "burning" sensation in a burn wound returning the patient's perception of the temperature of the wound to a perceived normal body temperature. Additionally, extract derived from *Aloe Barbadensis Miller* increases circulation in the minutest blood vessels in the skin and kills bacteria thereby escalating and facilitating burn wound healing.

While extracts derived from other species of *aloe vera* (over 550 species) have many of the properties of the extract derived from *Aloe Barbadensis Miller* these other species do not have all of the healing and soothing properties of *Aloe Barbadensis Miller*. Thus, extract derived from species other than that of *Aloe Barbadensis Miller* would negate the full effect of the burn wound composition on the tissue of the burn wound.

Moreover, the *aloe vera* extract used in the burn wound composition derived from *Aloe Barbadensis Miller*, cultivated or grown in the south eastern United States (e.g., North Carolina, South Carolina, Georgia, and Florida) provides a unique chemical composition from other extracts of *aloe vera* grown in other regions. The extract derived from *Aloe Barbadensis Miller* cultivated in regions other than the south eastern United States provides for differing chemical components that can affect the efficacy of the burn wound composition.

In certain embodiments, *aloe vera* used in the burn wound composition may include, by weight percent, based on the total weight of the burn wound composition, 0.1% to 10%, or any sub-range subsumed therein, such as for example, 3% to 7%, or 4% to 6%. In certain embodiments, *aloe vera* used in the burn wound composition may include, by weight percent, based on the total weight of the burn wound composition, 3%, 4%, 5%, 5.1%, 5.13%, 5.2%, 5.3%, 5.4%, 5.5%, 6%, or 7%.

Separately the ingredients used in the burn wound composition (leaf lard, yellow beeswax, Oil of Spike, pine rosin, and *aloe vera*) have been observed to have varied healing properties that are powerful enough to reduce pain but not completely eliminate it. Nor can any one of these ingredients, independently of the others, stop blistering and restore the skin tissue to its original state. However, when the ingredients of leaf lard, yellow beeswax, Oil of Spike, pine rosin, and *aloe vera* are combined as directed herein they become a synergistic burn wound composition in the realm of pain elimination, psychological, and physical pain relief, and provide time sensitive healing of the wounded skin. The burn wound composition increases the effectiveness of the power of healing, insuring the healing process without fail for first, second, and third degree burns. The three more powerful ingredients within the burn wound composition that eliminate pain and blistering are yellow beeswax, Oil of Spike, and pine rosin. The leaf lard and *aloe vera* while maintaining these properties in a powerful way have been observed by the inventor to implement and maintain healthy skin rejuvenation.

The inventor was surprised that the combination of components found in the burn wound composition was effective for treatment of burn wounds. In fact, the inventor was initially concerned that mixing the ingredients of leaf lard, yellow beeswax, Oil of Spike, pine rosin, and *aloe vera* extract together would be ineffective, or that one ingredient would negate the effect of another ingredient. For example, the presence of camphor in a burn wound composition is generally contraindicated due to the intensity of its counter irritating properties and its systemic toxicity. However, in practice, the inventor unexpectedly discovered that these five ingredients specifically mixed and heated as described herein to form the burn wound composition synergistically enhance one another's quality and ability for complete pain elimination and flesh healing of the burn wound.

It is contemplated that the burn wound composition can be formulated for and delivered by carriers. For example, carriers such as additives can be added to enhance or modify the color, the fragrance, the viscosity, increase shelf life, and generally produce a desired effect.

The burn wound composition can be stored in environments where temperatures range from −20° F. (−28.9° C.) to 120° F. (48.9° C.), or any sub-range subsumed therein, for example, from 0° F. (−17.8° C.) to 100° F. (37.8° C.), from 20° F. (−6.67° C.) to 90° F. (32.2° C.), from 30° F. (−16.1° C.) to 80° F. (26.7° C.), or from 40° F. (4.44° C.) to 70° F. (21.1° C.). In certain embodiments, the burn wound composition can be stored in environments where humidity ranges from 1% humidity to 99% humidity, or any sub-range subsumed therein, for example, from 10% to 90%, from 20% to 80%, or from 30% to 70%.

Further, the burn wound composition is highly stable retaining it's healing and pain relief properties for at least ten years without any reduction in its efficacy. The inventor was surprised to discover the unexpected fact that the burn wound compound can be stored for long periods of time, without losing its potency or becoming contaminated, in virtually any conditions, making the burn wound composition different than conventional burn salves available as those salves generally include ingredients or properties that do not allow for random storage but promote spoilage and contamination. In certain embodiments, the burn wound composition does not require an expiration date. The burn wound composition will conform to its environment (i.e. in colder temperatures it will be firmer than in warmer temperatures) but will remain soft enough under ambient conditions to use directly on the burn wound as a bandage without discomfort to the patient.

Being capable of storage in all kinds of humidity and temperature conditions makes the burn wound composition ideal for use in long expeditions in adverse environments such as military maneuvers, sporting genres, wilderness excursions, sailing voyages, space, and the like, or any combination thereof. The burn wound composition would give a phenomenal advantage to first responders such as paramedics, firefighters, and police. Further, the burn wound composition would be a valuable asset to hospitals and other health institutions, restaurants, all types of small businesses, and the industrial sector would benefit from it greatly. In fact, it would be of immense benefit in all commercial or private first aid kits. Burn wounds are not only very damaging physically they are very damaging psychologically and this burn wound composition can and will bring relief to both injuries. Some of the ingredients within the burn wound composition have preservative properties and calming effects thereby obviating the need for most, if not any, additives.

Conventional burn salves on the market cannot provide the same pain relief and healing properties as they have other ingredients in them that produce side effects, and as mentioned above, include limited storage requirements, and other ingredients that corrupt the healing powers of their ingredients. They also use ingredients that are not claimed to be pure extracts. As used herein, the term "pure" refers to a compound, component, or ingredient that is not chemically processed, bleached, or altered before use as an ingredient in the burn wound composition.

In addition to the burn wound compositions described in this specification, the present invention includes a process or method of making a burn wound composition. In one example, the method of making the burn wound composition can comprise melting the leaf lard in a container over a heat source, dissolving the yellow beeswax into the melted leaf lard to form a first mixture, mixing the pine rosin into the first mixture comprising the yellow beeswax and the leaf lard to form a second mixture, and adding the Oil of Spike and the *aloe vera* to the second mixture by stirring to form the burn wound composition. In certain embodiments, the method can further include removing the burn wound composition from the heat source, pouring the burn wound composition into a second container, and solidifying the burn wound composition in the second container. In certain embodiments, the method of making the burn wound composition can include making a burn wound composition wherein the leaf lard consists of leaf lard derived from pigs of the species *Sus scrofa domesticus*, the yellow beeswax consists of yellow beeswax derived from honey bees of the genus Apis, the Oil of Spike consists of Oil of Spike derived from *Lavandula latifolia*, the pine rosin consists of pine rosin derived from southern yellow pine trees of the genus *Pinus*, and the *aloe vera* consists of *aloe vera* extract derived from *Aloe Barbadensis Miller*. In certain embodiments, the method may produce a burn wound composition consisting of, by total weight of the burn wound composition, at least 30% leaf lard, 5-15% yellow beeswax, 0.5-10% Oil of Spike, 20-40% pine rosin, and 0.1-10% *aloe vera*.

In addition to the burn wound compositions and methods of making the burn wound composition described in this specification the present invention includes a method of treating a burn wound with a burn wound composition. In one example, the method of treating a burn wound comprises applying to a burn wound a first layer of the burn wound composition, applying to the burn wound a second layer of the burn wound composition, and not covering the burn wound or the applied first and second layers of the burn wound composition. In certain embodiments, the method can further comprise applying to the burn wound a third layer of the burn wound composition. In certain embodiments, the method of treating a burn wound includes application of a burn wound composition that consists of, by total weight of the burn wound composition, at least 30% leaf lard, 5-15% yellow beeswax, 0.5-10% Oil of Spike, 20-40% pine rosin, and 0.1-10% *aloe vera*. In certain embodiments, the method of treating a burn wound includes application of a burn wound composition that consists of, by total weight, 50-53% leaf lard, 9-11% yellow beeswax, 1-4% Oil of Spike, 29-32% pine rosin, and 4-6% *aloe vera*. In certain embodiments, the method of treating a burn wound includes application of a burn wound composition that consists of leaf lard derived from pigs of the species *Sus scrofa domesticus*, yellow beeswax derived from honey bees of the genus Apis, Oil of Spike derived from *Lavandula latifolia*, pine rosin derived from southern yellow pine trees of the genus *Pinus*, and *aloe vera* extract derived from *Aloe Barbadensis Miller*.

In certain embodiments, the method of treating a burn wound can include applying the first layer of the burn wound composition to the burn wound within a half hour of receiving the burn wound. The method of application of the burn wound composition to the burn wound depends on the type and severity of the burn. The burn wound area does not have to be cleaned before application of the burn wound composition. Once applied to the burn wound the burn wound composition will work its way under any detritus gently separating it from the epidermis without damaging it. This aspect of the burn wound composition is very important as it eliminates pain the victim would otherwise suffer from disturbing the tissues of the burn wound in an unnecessary cleaning procedure. The burn wound composition can be applied gently, with the hand, and directly onto the burned area and can be applied in a thinner film for minor burns or in a thicker layer for more severe burns. For example, a thinner layer having a thickness of 0.25-1.25 millimeters (e.g., about 1/32 inch (0.7938 mm)) may be suitable for minor burns, and a thicker layer having a thickness of 1.25-2 millimeters (e.g., about 1/16 inch (1.5875 mm)) may be suitable for more severe burns. It is understood, however, that the thickness of a layer of applied burn wound composition is not necessarily limited to any particular value for effectiveness. The burn wound composition should not be applied using a utensil, as that has the very high possibility of further injury to the burn wound.

The fragrance of the burn wound composition produces a calming effect to the patient thereby reducing the shock and stress from the injury. After the first application of the burn wound composition to the burn wound, the pain is removed and the formation of blisters is suppressed. A second application of the burn wound composition should be applied to the burn wound within fifteen to thirty minutes or when the burn wound composition disappears into the wound. The time for application of the second layer of the burn wound composition depends on the type and degree of burn as the more severe the burn the quicker the burn wound composition will be absorbed. For more severe burns a third or fourth application should be applied. Even though it may appear that one or two application layers have healed the burn, it is necessary to apply a third layer as once the burn wound composition is absorbed and the pain and blistering relieved one tends to think all is well when in reality the healing process is still being carried out in the dermis and hypodermis, the two layers of skin below the epidermis, or top layer of skin.

Once the burn wound composition is applied, the burn wound should not be covered. The burn wound composition efficacy is diminished by contact with a bandage. For example, should the burn wound composition be in direct contact with a bandage, the bandage can absorb and remove quantities of the burn wound composition from contact with the injured tissue. Additionally, direct contact of the burn wound and burn wound composition with a bandage can limit the exposure of the injured tissue to oxygen needed for healing. Thus, the use of a non-absorbing covering not in contact with the burn wound (or burn wound composition) can prevent further physical injury and promote wound healing. In one embodiment, the treated burn wound should not be exposed to heat such as sunshine or a hot shower. For example, exposure to a hot shower can increase inflammation and burn wound pain, remove the burn wound composition from contact with the wound site, and prevent burn wound healing using the burn wound composition. However, a patient's activity does not need to be stopped as long as the treated burn wound does not suffer further physical injury or where the burn is so severe that it causes respiratory or cardiac complications.

When the burn wound composition is used as directed the skin will become soft and as supple as before the burn occurred and the healed wounded skin will exhibit the same flexibility and stretching properties as it exhibited before the burn wound without pain or splitting. With use of the burn wound composition on the burn wound no granulation tissue is formed and the original flesh is substantially healed. The burn wound composition can be applied to the burn wound at any time after the burn. However, application of the burn wound composition to the burn wound at the early stages of the healing process will promote faster healing.

WORKING EXAMPLES

The following working examples are intended to further describe the invention. It is understood that the invention described in this specification is not necessarily limited to the examples described in this section.

Example 1

After a patient's second degree burn from a propane torch a burn wound composition was prepared for treatment of the burn wound. The burn wound composition was prepared by mixing the following components, by weight, 2.0 ounces (56.7 g) of unsalted butter was mixed with about 2.0 ounces (56.7 g) of Aloe *Arborescens* extract heating at a temperature of no more that 120° F. for about 8 minutes, stirring intermittently, and then cooling to room temperature (25° C.).

Approximately 0.24 g of the burn wound composition was applied directly to the burn wound using the hand and covering about 31.7525 mm in diameter and overlapping the burn area by about two times the diameter of the burn wound to ensure proper coverage of the burn wound. The burn wound composition of Example 1 produced a thin runny composition consistency. Due to the thin consistency the applied layers of burn wound composition were extremely thin resulting in a layer of approximately 0.3500 mm thickness. Four layers of the burn wound composition (each layer of about 0.24 g) were applied to the burn wound totaling about one gram of the burn wound composition. The first two layers of the burn wound composition were applied to the burn wound approximately 5 minutes apart and the second two layers were applied 10 minutes apart. However, the burn wound composition of Example 1 produced very little pain relief and did not prevent blistering.

Example 2

In an effort to improve the burn wound composition of Example 1 another burn wound composition was produced. The burn wound composition was prepared by mixing the following components, by weight, 2.0 ounces (56.7 g) of vegetable oil (e.g., 1.0 ounce canola oil and 1 ounce olive oil) was mixed with 2.0 ounces (56.7 g) Aloe *Arborescens* extract heating at a temperature of no more that 120° F. for about 8 minutes, stirring intermittently, and then cooling to room temperature (25° C.). Four layers of the burn wound composition were directly applied to the burn wound using the hand and fingers at intervals of five minutes apart resulting in a thickness of no more than 0.2500 mm. Again, the burn wound composition of Example 2 produced very little pain relief, did not prevent blisters from forming, and again produced a thin runny composition consistency.

Example 3

In another effort to improve the burn wound composition of Example 1 another burn wound composition was produced. The burn wound composition was prepared by mixing the following components, by weight, about 2.0 ounces (56.7 g) of leaf lard was mixed with 2.0 ounces (56.7 g) of Aloe *Arborescens* extract heating at a temperature of no more that 120° F. for about 10 minutes, stirred intermittently, and then cooled to room temperature (25° C.). The burn wound composition was directly applied to the burn wound with the hand and fingers using the same amounts and techniques as described in Example 2 with a layer thickness of the burn wound composition over the burn wound of about 0.2500 mm. Again, this burn wound composition produced very little pain relief, did not prevent blisters from forming, and produced a thin runny composition consistency.

Example 4

In an effort to make a burn wound composition with a thicker consistency than in Examples 1-3, another burn wound composition was produced. The burn wound composition was prepared by mixing the following components, by total weight, 1.0 ounce (28.3 g) of yellow beeswax, 3.0 ounces (85.0 g) leaf lard, 2.0 ounces (56.7 g) of *Aloe Barbadensis Miller* extract, and 1.0 ounce (28.3 g) of pine rosin heating at a temperature of no more that 120° F. for about 10 to 12 minutes, stirring intermittently, and then cooling to room temperature (25° C.).

The prepared burn wound composition was directly applied to the burn wound using the hand and fingers. The burn wound composition exhibited a thicker consistency than that observed in Examples 1-3 with a layer thickness of about 0.3500 mm. However, the burn wound composition continued to exhibit a consistency too thin to remain static over the burn wound. Although, the burn wound composition of Example 4 did not treat or relieve pain from the burn wound, the burn wound composition maintained skin flexibility and removed redness from the first degree burns quickly after repeated applications of three layers applied at five minute intervals. However, the total thickness of all layers of the burn wound composition was minimal (about 0.3500 mm) because much of the burn wound composition ran off of the burn wound site and some of the burn wound composition was absorbed into the skin.

Example 5

In order to treat a second degree burn a previously prepared burn wound composition was applied to the burn wound. Before use, the burn wound composition was stored for about three months at room temperature in a sealed container preventing light exposure.

The burn wound composition was originally prepared by mixing the following components, by total weight, 1.0 ounce (28.3 g) of yellow beeswax, 4.0 ounces (113.4 g) leaf lard, 1.0 ounce (28.3 g) of *Aloe Barbadensis Miller* extract, and 2.0 ounces (56.7 g) of pine rosin was mixed over low heat. The burn wound composition consistency was soft and firm, yet fluid. The burn wound composition was applied in direct contact with the burn wound using the hand and fingers in a thin layer of about 0.4500 mm. The first layer was applied five minutes after the injury and the following two layers (each layer having a thickness of about 0.4500 mm) were applied at 30 minute intervals. Due to the viscosity of the burn wound composition and absorption into the burn wound and surrounding tissue, the application of the three layers of burn wound composition resulted in a final a layer of about 0.4500 mm. Although the burn wound composition retarded blister formation it provided little pain relief.

Example 6

In an effort to improve the pain relieving aspects of the burn wound composition of Example 5, a burn wound composition was prepared for application to a burn wound. The burn wound composition was prepared by mixing the following components, by total weight, 1.0 ounce (28.3 g) yellow beeswax, 4.0 ounces (113.4 g) leaf lard, 1.0 ounce (28.3 g) *Aloe Barbadensis Miller* extract, 2.0 ounces (56.7 g) pine rosin, and 0.5 ounce (14.2 g) plant oil was mixed intermittently while the compounds were melting, over low heat (not exceeding 120° F.) for about 15 minutes, and then cooled to room temperature (25° C.). The plant oil used was chosen from the group consisting of black peppermint oil, dandelion sap, lemon oil, clove oil, basil oil, Oil of Spike, goldenrod oil, *eucalyptus* oil, hyssop oil, rose extract, and rosemary oil. The burn wound composition was applied directly to the burn wound using the hand and fingers in three layers, each layer approximately 0.4500 mm in thickness and covering an area of about two times the diameter of the burn wound. The first layer of the burn wound composition was directly applied to the burn wound within five minutes of the injury. The additional two layers of the burn wound composition were applied at 30 minute intervals.

Much like the burn wound composition of Examples 1-5, the burn wound composition of Example 6 was runny and absorption of the composition into the burn wound was observed. The application of the final layer (having a thickness of about 0.4500 mm) resulted in a total burn wound composition thickness of about 0.5000 mm for all three layers.

The burn wound composition treatment resulted in a decrease in the pain experienced from the burn wound. Additionally, the inventor observed that the burn wound composition was not firm enough to remain static over the burn wound area. The inventor also discovered that the addition of the Oil of Spike to the burn wound composition provided soothing qualities to the olfactory senses and was relaxing to the mind providing emotional comfort to the patient.

Example 7

In an effort to improve the pain relieving aspects of the burn wound composition of Example 6, a previously prepared burn wound composition (prepared about was applied to a second degree burn wound. Before use, the burn wound composition was stored for about six months at room temperature in a sealed container preventing light exposure.

The burn wound composition was originally prepared by placing 10.0 ounces (283.5 g) of leaf lard in a double boiler over a heat source of 130° F. (54.4° C.). Once the leaf lard was thoroughly melted, 2.0 ounces (56.7 g) of yellow beeswax was added to the leaf lard, stirring occasionally to let it dissolve into the leaf lard. Next, 6.0 ounces (170.1 g) of pine rosin was added to the mixture with gentle stirring until all of the ingredients were thoroughly dissolved and mixed. Then 0.5 ounce (14.2 g) of Oil of Spike and 1.0 ounce (28.3 g) *aloe vera* extract were added with gentle stirring until all ingredients were mixed into a consistent brown liquid over about 15 minutes. The burn wound composition was removed from the heat source and allowed to cool at ambient temperature (25° C.) for 10 minutes. The cooled burn wound composition was poured into an open storage container and allowed to solidify into a cream before sealing and storing. The burn wound composition was found not to be water soluble.

Approximately one gram of the burn wound composition was applied directly to the burn wound using the hand and fingers to create a layer of about 0.7938 mm within about five minutes following the burn injury. Second and third layers (each layer about 0.7938 mm in thickness) of the burn wound composition were applied directly to the burn wound at 30 minute intervals. As in Examples 1-6, the burn wound composition was applied in an area over the burn wound in a diameter approximately two times the diameter of the burn wound to ensure burn wound coverage. The inventor discovered that the viscosity of the burn wound composition of Example 7 was much thicker than that observed in Examples 1-6, and resulted in a composition that could be applied in thicker layers of up to 1.5875 mm for more severe burns, if needed.

The inventor discovered that there was a distinct difference in the efficacy of the burn wound composition by adding the Oil of Spike to the mixture during the heating process. For example, the inventor noticed that the addition of the Oil of Spike at the end of the heating process did not provide for the elimination of pain from the burn wound. However, the inventor discover that by adding the Oil of Spike followed by heating and mixing the burn wound composition at a temperature of 130° F. (54.4° C.) for 15 minutes, the burn wound composition, once applied to the burn wound, provided for substantial elimination of burn wound pain.

The inventor also was surprised to note that heating of the burn wound composition for longer periods would reduce the efficacy of the burn wound composition. For example, the inventor observed that heating of the burn wound composition for an hour rather than 15 minutes resulted in significant evaporation reducing the potency of the burn wound composition.

The inventor also observed that sterile conditions are not required for making and using the burn wound composition. For example, aseptic conditions are not required for handling, preparing, or applying the burn wound composition as the ingredients themselves are antiseptic.

The inventor observed that the burn wound composition acts as a bandage and should be left open without any further bandages or coverings over the burn wound composition. The inventor discovered, rather unexpectedly, that the burn wound treated with the burn wound composition and not covered eliminated the loss of skin and promoted healing.

The inventor was surprised to note that following treatment of the burn wound with the burn wound composition the skin did not scab over causing tightness, dryness, and exacerbating pain. In fact, the inventor observed that the components of the burn wound composition complement each other allowing them to work in unison, synergistically, to eliminate pain and heal burn wounds within hours instead of days.

The completed burn wound composition of Example 7 was found to substantially eliminate pain and to prevent blister formation on first, second, and third degree burn wounds. Further, the burn wound composition stopped the bleeding from third degree burn wounds, and kept the burn wound clean allowing it to heal faster. The burn wound composition provided healing to the burn wound that returned the skin to its original and normal state, free from scarring and disfiguration of the skin. The burn wound composition was used to treat both first, second, and third degree burns with successful healing free from blistering, pain, and disfiguration of the skin. The inventor observed that the amount of burn wound composition used to treat the burn wound depended on the amount of tissue exposed after each layer of the burn wound composition was absorbed into the burn wound and how much inflammation was present. For example, where a single layer of burn wound composition was rapidly absorbed into the wound exposing injured tissue above the layer of burn wound composition, a second layer of burn wound composition was applied.

In one instance of treating a second degree chemical burn, the burn wound composition had been prepared and stored for six years at ambient temperature (25° C.) and was applied directly to the second degree burn wound (using the hands and fingers) in three layers, with each layer having a thickness of about 0.7938 mm. The burn wound composition was applied directly to the second degree burn wound within five minutes of the injury in a layer of about 0.7938 mm covering approximately twice the diameter of the burn wound to ensure complete wound coverage. Second and third layers (each layer about 0.7938 mm in thickness) of the burn wound composition were applied to the burn wound at 30 minute intervals. The burn wound composition successfully eliminated the pain and redness from the second degree burn wound after about ten minutes, and at the end of about 1.5 hours the skin showed no harm or blisters.

In another instance of treating a second degree burn from a hot lawn mower muffler, the burn wound composition had been prepared and stored for twenty five years at ambient temperature (25° C.). The burn wound composition was directly applied to the burn wound in layers, each of about 0.7938 mm thickness, for a total of three application layers. The application of the three layers of the burn wound composition were applied directly to the burn wound using the methods described above for the second degree burn resulting from a chemical burn. Each layer of burn wound composition was absorbed into the skin before the subsequent application of the next layer was applied. The burn wound composition successfully eliminated the pain and redness from the burn wound after ten minutes and returned the skin to its normal state of suppleness after about 1.5 hours.

Various features and characteristics are described in this specification to provide an understanding of the composition, structure, production, function, and/or operation of the invention, which includes the disclosed compositions, methods, and processes. It is understood that the various features and characteristics of the invention described in this specification can be combined in any suitable manner, regardless of whether such features and characteristics are expressly described in combination in this specification. The inventor and the Applicant expressly intend such combinations of features and characteristics to be included within the scope of the invention described in this specification. As such, the claims can be amended to recite, in any combination, any features and characteristics expressly or inherently described in, or otherwise expressly or inherently supported by, this specification. Furthermore, the Applicant reserves the right to amend the claims to affirmatively disclaim features and characteristics that may be present in the prior art, even if those features and characteristics are not expressly described in this specification. Therefore, any such amendments will not add new matter to the specification or claims, and will comply with written description, sufficiency of description, and added matter requirements, including the requirements under 35 U.S.C. § 112(a) and Article 123(2) EPC.

Any numerical range recited in this specification describes all sub-ranges of the same numerical precision (i.e., having the same number of specified digits) subsumed within the recited range. For example, a recited range of "1.0 to 10.0" describes all sub-ranges between (and including) the recited minimum value of 1.0 and the recited maximum value of 10.0, such as, for example, "2.4 to 7.6," even if the range of "2.4 to 7.6" is not expressly recited in the text of the specification. Accordingly, the Applicant reserves the right to amend this specification, including the claims, to expressly recite any sub-range of the same numerical precision subsumed within the ranges expressly recited in this specification. All such ranges are inherently described in this specification such that amending to expressly recite any such sub-ranges will comply with written description, sufficiency of description, and added matter requirements, including the requirements under 35 U.S.C. § 112(a) and Article 123(2) EPC. Also, unless expressly specified or otherwise required by context, all numerical parameters described in this specification (such as those expressing values, ranges, amounts, percentages, and the like) may be read as if prefaced by the word "about," even if the word "about" does not expressly appear before a number. Additionally, numerical parameters described in this specification should be construed in light of the number of reported significant digits, numerical precision, and by applying ordinary rounding techniques. It is also understood that numerical parameters described in this specification will necessarily possess the inherent variability characteristic of the underlying measurement techniques used to determine the numerical value of the parameter.

The invention(s) described in this specification can comprise, consist of, or consist essentially of the various features and characteristics described in this specification. The terms "comprise" (and any form of comprise, such as "comprises" and "comprising"), "have" (and any form of have, such as "has" and "having"), "include" (and any form of include, such as "includes" and "including"), and "contain" (and any form of contain, such as "contains" and "containing") are open-ended linking verbs. Thus, a composition, coating, or process that "comprises," "has," "includes," or "contains" one or more features and/or characteristics possesses those one or more features and/or characteristics, but is not limited to possessing only those one or more features and/or characteristics. Likewise, an element of a composition, coating, or process that "comprises," "has," "includes," or "contains" one or more features and/or characteristics possesses those one or more features and/or characteristics, but is not limited to possessing only those one or more features and/or characteristics, and may possess additional features and/or characteristics.

The grammatical articles "a," "an," and "the," as used in this specification, including the claims, are intended to include "at least one" or "one or more", unless otherwise indicated. Thus, the articles are used in this specification to refer to one or more than one (i.e., to "at least one") of the grammatical objects of the article. By way of example, "a component" means one or more components, and thus, possibly, more than one component is contemplated and can be employed or used in an implementation of the described compositions, coatings, and processes. Nevertheless, it is understood that use of the terms "at least one" or "one or more" in some instances, but not others, will not result in any interpretation where failure to use the terms limits objects of the grammatical articles "a," "an," and "the" to just one. Further, the use of a singular noun includes the plural, and the use of a plural noun includes the singular, unless the context of the usage requires otherwise.

Any patent, publication, or other document identified in this specification is incorporated by reference into this specification in its entirety unless otherwise indicated, but only to the extent that the incorporated material does not conflict with existing descriptions, definitions, statements, illustrations, or other disclosure material expressly set forth in this specification. As such, and to the extent necessary, the express disclosure as set forth in this specification supersedes any conflicting material incorporated by reference. Any material, or portion thereof, that is incorporated by reference into this specification, but which conflicts with existing definitions, statements, or other disclosure material set forth herein, is only incorporated to the extent that no conflict arises between that incorporated material and the existing disclosure material. Applicant reserves the right to amend this specification to expressly recite any subject matter, or portion thereof, incorporated by reference. The amendment of this specification to add such incorporated subject matter will comply with written description, sufficiency of description, and added matter requirements, including the requirements under 35 U.S.C. § 112(a) and Article 123(2) EPC.

What is claimed is:

1. A burn wound composition consisting of, by total weight:
   46% to 56% leaf lard derived from pigs of the species *Sus scrofa domesticus;*
   5% to 15% yellow beeswax derived from honey bees of the genus *Apis;*

0.5% to 5% Oil of Spike derived from *Lavandula latifolia*;

25% to 35% pine rosin derived from southern yellow pine trees of the genus *Pinus*; and 0.1% to 10% *aloe vera* extract derived from *Aloe Barbadensis Miller*.

2. The burn wound composition of claim 1, wherein the composition consists of, by total weight:

49% to 53% leaf lard derived from pigs of the species *Sus scrofa domesticus*;

8% to 12% yellow beeswax derived from honey bees of the genus Apis;

1% to 4% Oil of Spike derived from *Lavandula latifolia*;

28% to 33% pine rosin derived from southern yellow pine trees of the genus *Pinus*; and 3% to 7% *aloe vera* extract derived from *Aloe Barbadensis Miller*.

3. A burn wound composition consisting of:
leaf lard;
yellow beeswax;
Oil of Spike;
pine rosin; and
*aloe vera*.

4. The burn wound composition of claim 3, wherein the leaf lard consists of leaf lard derived from pigs of the species *Sus scrofa domesticus*.

5. The burn wound composition of claim 3, wherein the yellow beeswax consists of yellow beeswax derived from honey bees of the genus Apis.

6. The burn wound composition of claim 3, wherein the Oil of Spike consists of Oil of Spike derived from *Lavandula latifolia*.

7. The burn wound composition of claim 3, wherein the pine rosin consists of pine rosin derived from southern yellow pine trees of the genus *Pinus*.

8. The burn wound composition of claim 7, wherein the pine rosin consists of rosin derived from at least one of *Pinus taeda* (loblolly pine), *Pinus palustris* (longleaf pine), *Pinus echinata* (shortleaf pine), and *Pinus elliottii* (slash pine).

9. The burn wound composition of claim 3, wherein the *aloe vera* consists of *aloe vera* extract derived from *Aloe Barbadensis Miller*.

10. The burn wound composition of claim 3, consisting of, by total weight of the composition, at least 30% leaf lard, 5-15% yellow beeswax, 0.5-10% Oil of Spike, 20-40% pine rosin, and 0.1-10% *aloe vera*.

11. A method of making the burn wound composition of claim 3 comprising:

melting the leaf lard in a container over a heat source;

dissolving the yellow beeswax into the melted leaf lard to form a first mixture;

mixing the pine rosin into the first mixture comprising the yellow beeswax and the leaf lard to form a second mixture; and adding the Oil of Spike and the *aloe vera* to the second mixture by stirring to form the burn wound composition.

12. The method of claim 11, further comprising removing the burn wound composition from the heat source, pouring the burn wound composition into a second container, and solidifying the burn wound composition in the second container.

13. The method of claim 11, wherein the leaf lard consists of leaf lard derived from pigs of the species *Sus scrofa domesticus*, the yellow beeswax consists of yellow beeswax derived from honey bees of the genus Apis, the Oil of Spike consists of Oil of Spike derived from *Lavandula latifolia*, the pine rosin consists of pine rosin derived from southern yellow pine trees of the genus *Pinus*, and the *aloe vera* consists of *aloe vera* extract derived from *Aloe Barbadensis Miller*.

14. The method of claim 11, wherein the burn wound composition consists of, by total weight of the burn wound composition, at least 30% leaf lard, 5-15% yellow beeswax, 0.5-10% Oil of Spike, 20-40% pine rosin, and 0.1-10% *aloe vera*.

15. A method of treating a burn wound comprising:

applying to a burn wound a first layer of the burn wound composition of claim 3;

applying to the burn wound a second layer of the burn wound composition of claim 3; and not covering the burn wound or the applied first and second layers of the burn wound composition.

16. The method of claim 15, further comprising applying to the burn wound a third layer of the burn wound composition.

17. The method of claim 15, wherein the burn wound composition consists of, by total weight:
at least 30% leaf lard,
5-15% yellow beeswax,
0.5-10% Oil of Spike,
20-40% pine rosin; and
0.1-10% *aloe vera*.

18. The method of claim 15, wherein the burn wound composition consists of, by total weight:
50-53% leaf lard,
9-11% yellow beeswax,
1-4% Oil of Spike,
29-32% pine rosin; and
4-6% *aloe vera*.

19. The method of claim 15, wherein the burn wound composition consists of:
leaf lard derived from pigs of the species *Sus scrofa domesticus*,
yellow beeswax derived from honey bees of the genus Apis,
Oil of Spike derived from *Lavandula latifolia*,
pine rosin derived from southern yellow pine trees of the genus *Pinus*, and
*aloe vera* extract derived from *Aloe Barbadensis Miller*.

20. The method of claim 15, wherein the applying of the first layer of the burn wound composition comprises applying the first layer of the burn wound composition to the burn wound within a half hour of receiving the burn wound.

* * * * *